United States Patent [19]

Wooden et al.

[11] Patent Number: 5,200,528

[45] Date of Patent: Apr. 6, 1993

[54] DIKETOPYRROLOPYRROLES

[75] Inventors: Gary Wooden, Oberschrot; Guy de Weck, Basel; Olof Wallquist, Marly, all of Switzerland

[73] Assignee: Ciba-Geigy Corporation, Ardsley, N.Y.

[21] Appl. No.: 870,986

[22] Filed: Apr. 20, 1992

[30] Foreign Application Priority Data

Apr. 26, 1991 [CH] Switzerland .......................... 1250/91

[51] Int. Cl.$^5$ .................. C07D 487/00; C07D 487/02
[52] U.S. Cl. .................................. 548/453; 544/106; 544/373; 546/199; 546/271
[58] Field of Search .............. 548/453; 544/106, 373; 546/199, 271

[56] References Cited

U.S. PATENT DOCUMENTS 4,791,204 12/1988 Jost et al. ........................ 548/101

FOREIGN PATENT DOCUMENTS 321919 6/1989 European Pat. Off. .
3832064 3/1990 Fed. Rep. of Germany .
3-26767 of 1991 Japan .

OTHER PUBLICATIONS

Chem. Abstract 111:196751y, 1987.
Chem. Abstract 113:61388f, 1988.

Primary Examiner—David B. Springer
Attorney, Agent, or Firm—JoAnn Villamizar

[57] ABSTRACT 1,4-Diketopyrrolo[3,4-c]pyrroles of formula

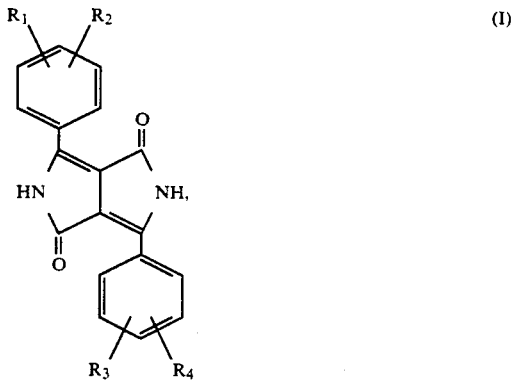

wherein $R_1$, $R_2$, $R_3$ and $R_4$ are each independently of one another hydrogen, Cl, Br, $CH_3$, $OCH_3$, CN or phenyl, and at least one of the substituents, $R_1$, $R_2$, $R_3$ and $R_4$ is a group $$-O(CH_2)_nX \text{ or } -O(CH_2CH_2O)_pCH_2CH_2X$$

wherein
n is an integer from 2 to 12, and
p is an integer from 1 to 3,
X is a heterocyclic radical selected from the group consisting of imidazolyl, pyrazolyl, triazolyl, piperazinyl, pyridinyl, pyrrolyl, thiazolyl, oxazolyl, benzoxazolyl, indolyl, benzthiazolyl, benzimidazolyl, benzotriazolyl, morpholinyl, piperidinyl and pyrrolidinyl, which radical is unsubstituted or substituted by one or two methyl groups, or is a group $$-NR_5R_6$$

or $$-N[(CH_2)_n-NR_5R_6]_2, \text{ wherein}$$

$R_5$ and $R_6$ are each independently of the other hydrogen, $C_1$-$C_6$ alkyl or $C_5$-$C_6$ cycloalkyl.

Pigment compositions comprising a minor amount of said compounds and diketopyrrolopyrrole pigments have excellent rheological and colouristic properties, especially in paint systems and in printing inks.

5 Claims, No Drawings

DIKETOPYRROLOPYRROLES

The present invention relates to novel diketopyrrolopyrroles which are substituted by at least one aminoalkoxy radical, and to the use thereof for enhancing the colouristic and rheological properties of diketopyrrolopyrrole pigments.

It is known that the properties of a pigment can be improved by addition thereto of a minor amount of a pigment which has been modified by the introduction of appropriate substituents. Thus, for example, DE-OS 38 32 064 discloses a process for the preparation of pigment compositions having enhanced colouristic and rheological properties by bead milling anthraquinone pigments in the presence of pigments which have been modified by substitution with specific aminoalkyl groups and which are defined as dispersants. Pigments which are substituted by a heterocyclic radical bound through a methylene group and which have enhanced flocculation stability and rheological properties are disclosed in EP-A 321 919. Diketopyrrolopyrrole compositions comprising a diketopyrrolopyrrole pigment and a minor amount of a modified diketopyrrole and having enhanced rheological properties are disclosed in U.S. Pat. No. 4,791,204. The modified diketopyrrolopyrroles are, inter alia, those which are substituted by cyclic carboxamide or dicarboxamide groups bound through a methylene group. Diketopyrrolopyrroles which are substituted by aminic radicals are disclosed in JP Kokai 91-26767 as pigment dispersants which result in enhanced rheological properties. The aminic radicals, however, are not bound through an alkoxy bridge.

Novel diketopyrrolopyrroles which are substituted by at least one aminoalkoxy radical have now been found which, admixed in a minor amount with diketopyrrolopyrrole pigments, lead to surprisingly good colouristic and rheological properties, especially in paint systems and printing inks.

Accordingly, the invention relates to 1,4-diketopyrrolo[3,4-c]pyrroles of formula

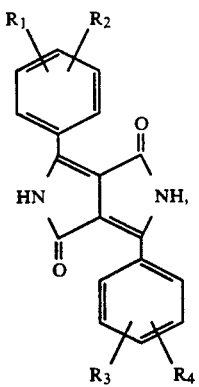

(I)

wherein $R_1$, $R_2$, $R_3$ and $R_4$ are each independently of one another hydrogen, Cl, Br, $CH_3$, $OCH_3$, CN or phenyl, and at least one of the substituents $R_1$, $R_2$, $R_3$ and $R_4$ is a group —O(CH$_2$)$_n$X or —O(CH$_2$CH$_2$O)$_p$CH$_2$CH$_2$X wherein
n is an integer from 2 to 12, and
p is an integer from 1 to 3, X is a heterocyclic radical selected from the group consisting of imidazolyl, pyrazolyl, triazolyl, piperazinyl, pyridinyl, pyrrolyl, thiazolyl, oxazolyl, benzoxazolyl, indolyl, benzthiazolyl, benzimidazolyl, benzotriazolyl, morpholinyl, piperidinyl and pyrrolidinyl, which radical is unsubstituted or substituted by one or two methyl groups, or is a group

—NR$_5$R$_6$ or

—N[(CH$_2$)$_n$—NR$_5$R$_6$]$_2$, wherein $R_5$ and $R_6$ are each independently of the other hydrogen, $C_1$–$C_6$alkyl or $C_5$–$C_6$cycloalkyl.

$R_5$ and $R_6$ defined as $C_1$–$C_6$alkyl may typically be methyl, ethyl, n-propyl, isopropyl, n-butyl, sec-butyl, tert-butyl, tert-amyl and n-hexyl.

$R_5$ and $R_6$ defined as $C_5$–$C_6$cycloalkyl are cyclopentyl and, preferably, cyclohexyl.

Particularly interesting 1,4-diketopyrrolo[3,4-c]pyrroles of formula I are those wherein at least one of $R_1$, $R_2$, $R_3$ or $R_4$ is a group —O(CH$_2$)$_n$X or —O(CH$_2$CH$_2$O)$_p$CH$_2$CH$_2$X wherein
n and p are as defined above, and X is a heterocyclic radical selected from the group consisting of imidazolyl, pyrazolyl, triazolyl, piperazinyl, pyridinyl, pyrrolyl, thiazolyl, oxazolyl, morpholinyl, piperidinyl and pyrrolidinyl, or is a group

—NR$_5$R$_6$ wherein $R_5$ and $R_6$ are as defined above.

Preferred 1,4-diketopyrrolo[3,4-c]pyrroles of formula I are those wherein one or two of $R_1$, $R_2$, $R_3$ or $R_4$ are a group —O(CH$_2$)$_n$X or —O(CH$_2$CH$_2$O)$_p$CH$_2$CH$_2$X wherein
n is an integer from 2 to 6 and
p is an integer from 1 or 2, and
X is a heterocyclic radical selected from the group consisting of imidazolyl, pyrazolyl, triazolyl, piperazinyl, pyridinyl, pyrrolyl, thiazolyl, oxazolyl, morpholinyl, piperidinyl and pyrrolidinyl, or is a group

—NR$_5$R$_6$ wherein $R_5$ and $R_6$ are each independently of the other hydrogen, methyl or ethyl.

Most preferably, X is a heterocyclic radical selected from the group consisting of imidazolyl, pyrazolyl, morpholinyl, piperidinyl, pyrrolidinyl and triazolyl, or is a group —NR$_5$R$_6$.

Particularly preferred 1,4-diketopyrrolo[3,4-c]pyrroles of formula I are those wherein one of $R_3$ or $R_4$ is a group —O(CH$_2$)$_n$NR$_5$R$_6$ or —O(CH$_2$)$_n$X wherein n is an integer from 2 to 4 and $R_5$ and $R_6$ are identical and are hydrogen, methyl or ethyl, and X is morpholinyl, piperidinyl or pyrrolidinyl.

As already previously mentioned, the admixture of a minor amount of a novel diketopyrrolopyrrole of formula I with a diketopyrrolopyrrole pigment effects a quite surprising enhancement of the colouristic and rheological properties of this latter.

The invention accordingly further relates to pigment compositions comprising a) 80–99.9% by weight of at least one 1,4-diketopyrrolo[3,4-c]pyrrole of formula I, wherein $R_1$, $R_2$, $R_3$ and $R_4$ are each independently of one another hydrogen, Cl, Br, $CH_3$, $OCH_3$, CN or phenyl, and b) 0.1–20% by weight of at least one 1,4-diketopyrrolo[3,4-c]pyrrole of formula I as defined in a) in which at least one of $R_1$, $R_2$, $R_3$ and $R_4$ is a group

as defined above.

The diketopyrrolopyrroles of component a) of the novel compositions are known compounds and can be conveniently prepared by the processes described in U.S. Pat. Nos. 4,579,949 and 4,749,795.

The diketopyrrolopyrroles of formula I can be prepared by processes analogous to standard known ones, typically by reacting a diester of succinic acid with a nitrile or with a mixture of nitriles of formulae

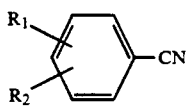

and

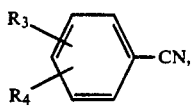

as taught e.g. in U.S. Pat. Nos. 4,579,949 and 4,720,305, or, especially in the case of the preferred compounds of formula I, wherein one of $R_3$ or $R_4$ is a group

by reacting a pyrrolinone of formula

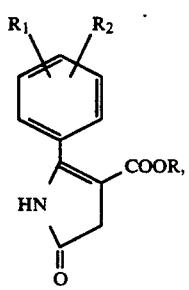

or an enamine of formula

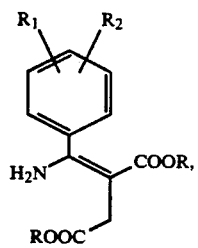

with a nitrile or with a mixture of nitriles of formula III, as disclosed e.g. in U.S. Pat. Nos. 4,659,775 and 4,749,795.

$R_1$, $R_2$, $R_3$ and $R_4$ in formulae II, III, IV and V are as defined above, with the proviso that at least one of said substituents, and preferably one of $R_3$ and $R_4$, must be a group

as defined above.

R in formulae IV and V is lower alkyl, typically methyl, ethyl, n-propyl, isopropyl, n-butyl, sec-butyl, tert-butyl and tert-amyl. Methyl and ethyl are preferred.

The compounds of formulae II, III, IV and V are known compounds. Any that are novel can be prepared by methods analogous to standard known ones.

The pigment compositions can be conveniently prepared by the following commonly employed methods:

Direct in the synthesis by reacting a diester of succinic acid with different nitriles of formulae II and III, as taught e.g. in U.S. Pat. No. 4,720,305, with the proviso that the nitrile not carrying the group

(or the mixture of such nitriles) must be used in such excess over the nitrile (or the mixture of such nitriles) carrying at least one of said groups that the required ratio defined above of a) to b) is maintained.

By mixing components 1 and 2 described below.

Component 1 consists of at least one 1,4-diketopyrrolo-[3,4-c]-pyrrole, as defined in a).

Component 2 consists either of at least one 1,4-diketopyrrolo[3,4-c]pyrrole as defined in b), or of a mixture of at least one 1,4-diketopyrrolo[3,4-c]pyrrole as defined in a) and at least one 1,4-diketopyrrolo[3,4-c]pyrrole as defined in b)

The two components 1 and 2 are mixed by any of the commonly employed methods. Component 2 can be admixed conveniently as moist press cake or as powder during the synthesis, the recrystallisation or the filtration of component 1 with this latter. Components 1 and 2 can also be mixed by intensive mixing or milling, or they can be added to the high molecular weight organic material to be coloured and mixed during the dispersion process.

The novel pigment compositions can be used as pigments for colouring organic material of high molecular weight.

Illustrative examples of organic materials of high molecular weight which can be coloured with the novel pigment compositions are cellulose ethers and esters, typically ethyl cellulose, nitrocellulose, cellulose acetate, cellulose butyrate, natural resins or synthetic resins, typically polymerisation or condensation resins, such as aminoplasts, preferably urea/formaldehyde and melamine/formaldehyde resins, alkyd resins, phenolic plastics, polycarbonates, polyolefins, polystyrene, polyvinyl chloride, polytetrafluoroethylene, polyamides, polyurethanes, polyesters, polyether ketones, polyphenylene oxides, rubber, casein, silicone and silicone resins, singly or in mixtures.

The above high molecular weight organic compounds may be singly or as mixtures in the form of plastics, melts or of spinning solutions, paints, coating materials or printing inks. Depending on the end use requirement, it is expedient to use the pigments of the invention as toners or in the form of preparations. The pigments of the invention can be used in an amount of 0.01 to 30% by weight, preferably 0.1 to 10% by weight, based on the high molecular weight organic material.

For pigmenting paints, coating materials and printing inks, the high molecular weight organic materials and the pigments of the invention, together with optional additives such as filters, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

The colourations obtained in plastics materials, fibres, paints systems or printing inks have good allround fastness properties such as superior colour strength, good dispersibility, good fastness to overspraying, migration, heat, light and weathering, and they have low viscosity and good gloss.

Furthermore, compared to unmodified base pigments, the novel pigment compositions have enhanced performance properties in application, such as enhanced rheology and shelf life, lesser separation effects, such as floating when concurrently using e.g. white pigments, and a lesser tendency to flocculate. Owing to the good rheological properties of these compositions it is also possible to prepare coating materials and paints systems with high loading. They are therefore preferably suitable for colouring paints, especially for metal effect finishes.

The above described component 2 may, however, itself also be used as pigment for colouring the organic materials of high molecular weight cited previously. For this utility it can be used as crude product or after appropriate conditioning/aftertreatment, conveniently as described above in connection with the novel pigment compositions.

The invention is illustrated by the following Examples.

EXAMPLE 1

2.3 g of sodium are stirred vigorously in 55 ml of refluxing tert-amyl alcohol until complete dissolution. The temperature is lowered to 95°–100° C., then 6.38 g of 4-[2-(dimethylamino)ethoxy]benzonitrile are added, followed by the addition over 45 minutes of 7.73 g of the pyrrolinone of formula

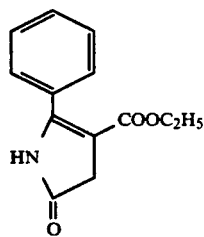

and stirring is continued for 2 hours at 95°–100° C. The reaction mixture is then cooled to 40° C. and poured into a stirred solution of 6.7 g of acetic acid in 500 ml of methanol. The crude product so obtained is isolated by filtration, washed with methanol and then with water and dried overnight at 90° C. Yield: 8.41 g (67% of theory) of the product of formula

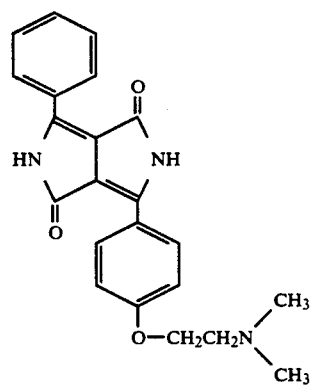

in the form of a yellowish-red powder.

Analysis: calcd: C 70.38% H 5.64% N 11.19%; found: C 70.11% H 5.64% N 11.17%.

EXAMPLE 2

In a sulfonating flask, 17.2 g of 3.6-diphenyl-1,4-diketopyrrolo[3,4-c]pyrrole is stirred as moist press cake (29.1%; 5.0 g of solids) in 100 ml of deionised water for 1 hour at room temperature. Then 0.24 g of the compound obtained in Example 1 is added as moist press cake (54%; 0.13 g of solids), and the suspension is stirred for 2 hours at room temperature and then filtered. The filter cake is dried under vacuum at 80° C., giving 5.2 g of a red pigment.

EXAMPLE 3

35 ml of dry tert-amyl alcohol and 1.38 g of sodium are charged to a 100 ml sulfonating flask and thoroughly mixed at 105° C. with efficient stirring for 17 hours until the sodium is completely reacted. Then 4.9 g of 4-(3-dimethylaminopropoxy)benzonitrile and 2.6 g of benzonitrile are added, followed by the dropwise addition over 80 minutes of 4.5 g of diisopropyl succinate. The reaction mixture is stirred for 2 hours at 110° C., then cooled to room temperature and charged to a cooled mixture of 0° C. of 70 ml of methanol/water 1:1 (vol.) and 3.43 ml of acetic acid in a 350 ml sulfonating flask. The mixture is stirred for 2 hours at room temperature, filtered, and the residue is washed with methanol and water and dried at 90° C. in a vacuum oven to give a dark red pigment. The following data are obtained by mass spectroscopic analysis (FD): m/e 288, 389, 490.

EXAMPLES 4–16

The procedure of Example 3 is repeated, using equivalent amounts of the corresponding nitriles to give the compounds listed in Table 1.

TABLE 1

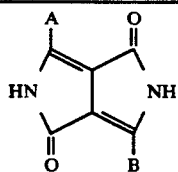

| Example | A | B | Mass spectrum | |
|---|---|---|---|---|
| 4 | phenyl | —C₆H₄—O—(CH₂)₃—N(morpholine) | m/e 288, 431 | (EI) |
| 5 | phenyl | —C₆H₃(Cl)—O—(CH₂)₃—N(CH₃)₂ | m/e 288, 423, 425 | (EI) |
| 6 | phenyl | —C₆H₄—O—(CH₂)₃—N(3,5-dimethylpyrazolyl) | m/e 288, 440, 592 | (FD) |
| 7 | 4-Cl-phenyl | —C₆H₄—O—(CH₂)₃—N(3,5-dimethylpyrazolyl) | m/e 356, 474, 592 | (FD) |
| 8 | phenyl | —C₆H₄—O—(CH₂)₂—N(CH₃)₂ | m/e 288, 375, 462 | (M⁻) (CI, NH₃) |
| 9 | 4-Cl-phenyl | —C₆H₄—O—(CH₂)₂—N(CH₃)₂ | m/e 357, 410, 463 | (M + H)⁺ (CI, NH₃) |
| 10 | phenyl | —C₆H₄—O—(CH₂)₆—N(CH₃)₂ | m/e 288, 431, 574 | (FD) |
| 11 | 4-Cl-phenyl | —C₆H₄—O—(CH₂)₆—N(CH₃)₂ | m/e 356, 465, 574 | (FD) |
| 12 | phenyl | —C₆H₄—O—(CH₂)₃—N(piperidine) | m/e 288, 429, 570 | (FD) |
| 13 | phenyl | —C₆H₄—O—(CH₂)₃—N[(CH₂)₂—N(C₂H₅)₂]₂ | m/e 288, 560, 831 | (FD) |

TABLE 1-continued

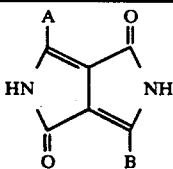

| Example | A | B | Mass spectrum | |
|---|---|---|---|---|
| 14 | —⟨phenyl⟩ | —⟨phenyl⟩—O—(CH₂)₂—O—(CH₂)₂—N(CH₃)₂ | $m/e$ 288, 419, 550 | (FD) |
| 15 | —⟨phenyl⟩ | —⟨phenyl⟩—O—(CH₂)₃—N(C₄H₉)₂ | $m/e$ 288, 473, 658 | (EI) |
| 16 | —⟨phenyl⟩ | —⟨phenyl⟩—O—(CH₂)₃—N(piperazinyl)—CH₃ | $m/e$ 288, 444 | (EI) |

EI = Electron Impact
FD = Field Desorption
CI = Chemical Ionisation

EXAMPLES 17 AND 18

The procedure of Example 3 is repeated such that in each case only one nitrile (corresponding to the radicals A in Table 2) is used, but in twice the equivalent amount, to give the compounds listed in Table 2.

TABLE 2

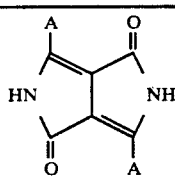

| | | Elemental analysis | | | | | |
|---|---|---|---|---|---|---|---|
| | | calculated | | | found | | |
| Example | A | C | H | N | C | H | N |
| 17 | —⟨phenyl⟩—O—(CH₂)₂—N(CH₃)₂ | 67.51 | 6.54 | 12.11 | 65.42 | 6.67 | 7.90 |
| 18 | —⟨phenyl⟩—O—(CH₂)₃—N(CH₃)₂ | 68.55 | 6.99 | 11.42 | 68.14 | 7.15 | 10.96 |

EXAMPLE 19

To determine the flow properties, the pigment treated as described in Example 2 is incorporated by a standard method into an alkyd paint system (®SETAL 84, Kunstharzfabrik Synthesis B. V., Holland; solids content: 70% by weight).

The flow properties of the paint formulation which contains 12% by weight of pigment and 54% by weight of total solids and the total pigment/binder ratio of which is 0.3, are determined with a HAAKE ®ROTO-VISCO RV 12 viscosimeter (measuring temperature: 25° C., measuring system: SV-SP, shear range: D=0–100 [1/s]).

Compared to untreated 3,6-diphenyl-1,4-diketopyrrolo[3,4-c]pyrrole, the red pigment obtained according to Example 2 has enhanced rheological properties in addition to excellent colouristic properties.

EXAMPLE 20

An offset printing ink is prepared on a three-roll mill by the method of DIN 53 238-12 with the pigment treated according to Example 2, namely with
20 parts of pigment and
80 parts of varnish comprising 50% parts by weight of oil-modified phenolic varnish (®ALVCO 1407)
32% parts by weight of terephthalic acid alkyd-linseed oil resin (100% solids content; ®TERLON 3)
18% parts by weight of mineral oil (boiling range 157°-214° C.; ®SUNOCO OIL).

The printing ink so obtained has excellent rheological properties and the prints produced therewith on art paper have surprisingly good colouristic properties (strong red shade).

What is claimed is:

1. A 1,4-diketopyrrolo[3,4-c]pyrrole of formula

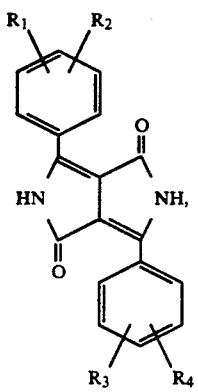

(I)

wherein $R_1$, $R_2$, $R_3$ and $R_4$ are each independently of one another hydrogen, Cl, Br, $CH_3$, $OCH_3$, CN or phenyl, and at least one of the substituents $R_1$, $R_2$, $R_3$ and $R_4$ is a group —O(CH$_2$)$_n$X or —O(CH$_2$CH$_2$O)$_p$CH$_2$CH$_2$X wherein n is an integer from 2 to 12, and
p is an integer from 1 to 3,
X is a heterocyclic radical selected from the group consisiting of piperazinyl, pyridinyl, morpholinyl, piperidinyl and pyrrolidinyl, which radical is unsubstituted or substituted by one or two methyl groups, or is a group

—NR$_5$R$_6$ or

—N[(CH$_2$)$_n$—NR$_5$R$_6$]$_2$, wherein $R_5$ and $R_6$ are each independently of the other hydrogen, $C_1$–$C_6$alkyl or $C_5$–$C_6$cycloalkyl.

2. A 1,4-diketopyrrolo[3,4-c]pyrrole of formula I according to claim 1, wherein at least one of $R_1$, $R_2$, $R_3$ or $R_4$ is a group —O(CH$_2$)$_n$X or —O(CH$_2$CH$_2$O)$_p$CH$_2$CH$_2$X wherein n and p are as defined in claim 1, and X is a heterocyclic radical selected from the group consisting of piperazinyl, pyridinyl, morpholinyl, piperidinyl and pyrrolidinyl, or is a group

—NR$_5$R$_6$ wherein $R_5$ and $R_6$ are as defined in claim 1.

3. A 1,4-diketopyrrolo[3,4-c]pyrrole of formula I according to claim 1, wherein one or two of $R_1$, $R_2$, $R_3$ or $R_4$ are a group —O(CH$_2$)$_n$X or —O(CH$_2$CH$_2$O)$_p$CH$_2$CH$_2$X wherein n is an integer from 2 to 6 and
p is an integer from 1 or 2, and
X is a heterocyclic radical selected from the group consisting of piperazinyl, pyridinyl, morpholinyl, piperidinyl and pyrrolidinyl, or is a group

—NR$_5$R$_6$ wherein $R_5$ and $R_6$ are each independently of the other hydrogen, methyl or ethyl.

4. A 1,4-diketopyrrolo[3,4-c]pyrrole according to claim 3, wherein X is a heterocyclic radical selected from the group consisting of morpholinyl, piperidinyl and pyrrolidinyl or is a group —NR$_5$R$_6$, wherein $R_5$ and $R_6$ are as defined in claim 3.

5. A 1,4-diketopyrrolo[3,4-c]pyrrole 3 of formula I according to claim 3, wherein one of $R_3$ or $R_4$ is a group —O(CH$_2$)$_n$NR$_5$R$_6$ or —O(CH$_2$)$_n$X wherein n is an integer from 2 to 4 and $R_5$ and $R_6$ are identical and are hydrogen, methyl or ethyl, and X is morpholinyl, piperidinyl or pyrrolidinyl.

* * * * *